United States Patent [19]

Mesens et al.

[11] Patent Number: 4,956,351
[45] Date of Patent: Sep. 11, 1990

[54] ANTIVIRAL PHARMACEUTICAL COMPOSITIONS CONTAINING CYCLODEXTRINS

[75] Inventors: Jean L. Mesens, Wechelderzande; Koenraad J. L. M. Andries, Beerse, both of Belgium

[73] Assignee: Janssen Pharmaceutica N.V. frame-543, Beerse, Belgium

[21] Appl. No.: 210,677

[22] Filed: Jun. 23, 1988

Related U.S. Application Data

[63] Continuation-in-part of Ser. No. 68,512, Jul. 1, 1987, abandoned.

[51] Int. Cl.$^5$ .......................... A61K 9/18; C08B 37/16
[52] U.S. Cl. .......................................... 514/58; 536/46; 536/103
[58] Field of Search ...................... 536/103, 46; 514/58

[56] References Cited

U.S. PATENT DOCUMENTS

| | | | |
|---|---|---|---|
| 4,289,783 | 9/1981 | Mesens | 514/400 |
| 4,599,327 | 7/1986 | Nógrádi et al. | 514/58 |
| 4,603,123 | 7/1986 | Chiesi et al. | 514/58 |
| 4,727,064 | 2/1988 | Pitha | 514/58 |
| 4,834,985 | 5/1989 | Elger et al. | 424/488 |

FOREIGN PATENT DOCUMENTS

| | | |
|---|---|---|
| 149197 | 7/1985 | European Pat. Off. . |
| 156433 | 10/1985 | European Pat. Off. . |
| 197571 | 10/1986 | European Pat. Off. . |

OTHER PUBLICATIONS

Al-Nakib, et al., Arch. Virology, 92, 255–260 (1987).
Al-Nakib, et al., J. Antimicrobial Chemoth., 20, 887–892 (1987).
Hayden, Antimicrobial Agents and Chemoth., June 1982, pp. 892–897.
23rd Interscience Con. Antimicrobial Agents Chemotherapy, Oct. 1983, Abstract 931.

*Primary Examiner*—Ronald W. Griffin
*Attorney, Agent, or Firm*—Charles J. Metz

[57] ABSTRACT

An antiviral composition for adminisitration to a mammal, in particular, intranasally, for the treatment of the common cold by control of common rhinoviruses. The composition is an inclusion complex of a cyclodextrin, e.g. an α-, β- or γ-cyclodextrin or derivatives thereof and an antiviral agent.

36 Claims, No Drawings

ANTIVIRAL PHARMACEUTICAL COMPOSITIONS CONTAINING CYCLODEXTRINS

CROSS-REFERENCE TO RELATED APPLICATIONS

This is a continuation-in-part of Ser. No. 68,512, filed July 1, 1987, now abandoned.

BACKGROUND OF THE INVENTION

The in vivo efficacy of known inhibitors of rhinovirus replication may not correspond well with their in vitro activity. Al-Nakib et al. have reported in the Archives of Virology 92, p. 255-260 (1987) that 4',6-dichloroflavan did not produce any consistent or significant reduction in clinical parameters of infection even though it has a marked antirhinoviral activity in tissue culture. However, the poor results obtained severely limit the usefulness of this apparently potent agent. Similarly, Al-Nakib et al. in Journal of Antimicrobial Chemotherapy 20, 887-892 (1987), report that the administration of the antiviral chalcone (RO 09-0410) did not reduce the incidence of infection or illness in vivo.

The need in the art for effective in vivo delivery of potent in vitro rhinovirus inhibitors is further shown by F. G. Hayden in Antimicrobial Agents and Chemotherapy, June 1982, p. 892-897. In this article, in vivo results of intranasal administration of enviroxime are disclosed as being no better than placebo even though concentrations of the drug were at least 50 times higher than the in vitro inhibitory concentrations.

Similarly, in vivo test results for the synthetic rhinovirus specific antiviral RMI-15,731 from Merrell Dow Pharmaceuticals were reported in Abstract 931 at the 23rd Interscience Con. Antimicrobial Agents Chemotherapy in Las Vegas, U.S.A., in October 1983. The clinical results showed that RMI-15,731 did not show significant prophylactic activity as compared to placebo.

The failure of agents active in vitro to prove out in vivo is particularly frustrating since high concentrations of the agents are found over the test period in the area of infection.

DESCRIPTION OF THE INVENTION

The present invention concerns pharmaceutical compositions for treating a mammal suffering from a viral infection, said pharmaceutical compositions containing an antiviral agent, and a cyclodextrin or a derivative thereof.

Such compositions may be deposited at the site of viral growth to supply effective concentrations for sustained periods until the mammalian body's natural immunological defenses attack and overcome the virus. They result in a low degree of irritation to sensitive mucous membrane and yet deliver in a continuous and controlled fashion sufficiently high concentrations of active antivirals to the site of infection.

In another aspect of the present invention there is provided a method of treating a mammal suffering from a viral infection, which method comprises the administration of an antivirally effective amount of a pharmaceutical composition containing an antiviral agent and a cyclodextrin or a derivative thereof.

As viral infections which can be treated with the pharmaceutical compositions of the present invention there may be mentioned infections caused by herpes viruses, influenza viruses, rotaviruses, coronaviruses, and in particular picornaviruses, preferably rhinoviruses, i.e. viruses responsible for the common cold.

The compositions are particularly convenient for treating local viral infections, in particular mucosal infections, e.g. pneumonal, nasal, vaginal, eye, oral or buccal infections and in particular mucosal infections at these parts of the body.

The said compositions are believed to be deposited or remain at the site of viral growth to supply effective concentrations of the active ingredient for sustained periods. In contrast herewith, Maitani et al. in Drug Design and Delivery, 1986, Vol. 1, pp. 65-70, describe the absorption through the nasal mucosa of $\beta$-interferon in combination with surfactants, in particular with a complex of 1-dodecylazacycloheptan-2-one and $\beta$-cyclodextrin.

The antiviral agents for use in the compositions of the present invention may be of various nature but in particular hydrophobic antiviral agents will preferably be used.

The cyclodextrin to be used in the composition and method of the present invention include any of those unsubstituted and substituted cyclodextrins known in the art, e.g. the unsubstituted $\alpha$-(hexamer), $\beta$-(heptamer and $\alpha$-(octamer)cyclodextrins. $\alpha$-Cyclodextrin or cyclohexaamylose consists of a torus containing six anhydroglucose units; the seven unit member is known as $\beta$-cyclodextrin or cycloheptaamylose and contains 7 anhydroglucose units; $\gamma$-cyclodextrin or cyclooctamylose contains 8 anhydroglucose units. When reference is made hereto the "torus molecule" or "cyclodextrins" it is intended that such terms include the foregoing forms as well as still other tori which have a still larger number of units in the molecule.

Substituted cyclodextrins which can be used in the invention include polyethers described in U.S. Pat. No. 3,459,731 which is incorporated by reference for the definition and processes for preparation. In general, unsubstituted cyclodextrins are reacted with an alkylene oxide, preferably under superatmospheric pressure and at an elevated temperature, in the presence of an alkaline catalyst. The reaction is preferably conducted in an autoclave at pressures of up to about 4.5 bar (or about 4.5 atm), or higher, and at temperatures of at least about 70° C. An amount of the alkylene oxide is added that is sufficient to accomplish the desired amount of addition to the anhydroglucose units in the torus molecule, that is, the cyclodextrin. The reaction is continued until the desired amount of alkylene oxide addition to cyclodextin has occurred. One way in which this can be determined is to note the point when the pressure is reduced in the autoclave. Following the reaction, the catalyst optionally may be neutralized, as by an acid addition, the polyether product may then be recovered. The alkylene oxides that can be used in the reaction with cyclodextrin include the lower alkylene oxides such as, for example, ethylene oxide, propylene oxide, butylene oxide, amylene oxide, glycidol (hydroxypropylene oxide), butadiene oxide, styrene oxide and the like. In the substituted cyclodextrin final product, one or more of the hydroxy moieties of the cyclodextrin products may be replaced by the following general formula:

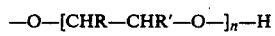

—O—[CHR—CHR'—O—]$_n$—H wherein R and R' are different or the same, and can be hydrogen, lower alkyl radicals, lower alkyl halides, lower alkyl alcohols, lower alkyl substituted by aryl, e.g. phenyl, lower alkenyl or aryl, e.g. phenyl. The lower alkyl or lower alkenyl may be up to about butyl or respectively butenyl, for example; n is an average number of alkylene oxide units per anhydroglucose and can range from less than 1 to about 50, or more, in particular from 1 to 20, more in particular from 1 to 10, or from 1 to 5.

Since a hydroxy moiety of the cyclodextrin can be substituted by an alkylene oxide which itself can react with yet another molecule of alkylene oxide, the average molar substitution (MS) is used as a measure of the average number of moles of the substituting agent per glucose unit. The MS can be greater than 3 and theoretically has no limit.

Further substituted cyclodextrins are ethers wherein the hydrogen of one or more cyclodextrin hydroxy groups is replaced by $C_{1-6}$alkyl, hydroxy $C_{1-6}$alkyl, carboxy $C_{1-6}$alkyl or $C_{1-6}$alkyloxycarbonyl $C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy $C_{2-4}$alkyl or carboxy$C_{1-2}$alkyl or more in particular by methyl, ethyl, hydroxyethyl, hydroxypropyl, hydroxybutyl, carboxymethyl or carboxyethyl. In the foregoing definitions the term "$C_{1-6}$-alkyl" is meant to include straight and branched saturated hydrocarbon radicals, having from 1 to 6 carbon atoms, such as, methyl, ethyl, 1-methylethyl, 1,1-dimethylethyl, propyl, 2-methylpropyl, butyl, pentyl, hexyl and the like.

Such ethers can be prepared by reacting the starting cyclodextrin with an appropriate O-alkylating agent or a mixture of such agents in a concentration being selected so that the desired cyclodextrin ether is obtained. The said reaction is preferably conducted in a suitable solvent in the presence of an appropriate base. An appropriate O-alkylating agent is, for example, an alkyl, hydroxyalkyl, carboxyalkyl or (alkyloxy-carbonyl)alkyl halide or sulfonate, e.g. methyl chloride, methyl bromide, methyl iodide, ethyl bromide, propyl methylsulfonate, ethyl chloroacetate, α-chloroacetic acid; or an oxirane, e.g. oxirane, methyloxirane. Suitable solvents are, for example, water: an alcohol or polyalcohol, e.g. methanol, ethanol, 1-propanol, 2-propanol, 1-butanol, 1,2-ethanediol, 1,2-propanediol and the like; a ketone, e.g. 2-propanone, 2-butanone, 4-methyl-2-pentanone, and the like; an ether or polyether, e.g. ethoxyethane, 2-(2-propyloxy)propane, tetrahydrofuran, 1,2-dimethoxyethane and the like; and $C_1$–$C_4$-alkyloxy-$C_2$–$C_3$-alkanol and mixtures of such solvents. An appropriate base is, for example, an alkali or earth alkaline metal hydroxide, e.g. sodium hydroxide, potassium hydroxide; or an alkali or earth alkaline metal hydride or amide, e.g. sodium hydride, calcium hydride, sodium amide and the like bases. Preferably, the said O-alkylation reaction is conducted with 0.1 to 3 parts by weight of water per part by weight cyclodextrin in case there is no organic solvent used, and with 1 to 40 parts by weight organic solvent per part by weight cyclodextrin in case no water is used. With such ethers, the degree of substitution (DS) is the average number of substituted hydroxy functions per glucose unit, the DS being thus 3 or less.

In the cyclodextrin derivatives for use in the compositions according to the present invention, the DS preferably is in the range of 0.125 to 3, in particular 0.3 to 2, more in particular 0.3 to 1, and the M.S. is in the range of 0.125 to 10, in particular of 0.3 to 3 and more in particular 0.3 to 1.5.

Other references describing cyclodextrins for use in the compositions according to the present invention, and which provide a guide for the preparation and characteristics of cyclodextrins, for the process of depositing the selected agent within the cyclodextrin molecule or the use of cyclodextrins in pharmaceutical compositions include the following:

"Cyclodextrin Chemistry" by M. L. Bender et al., Springer-Verlag, Berlin (1978); "Advances in Carbohydrate Chemistry", Vol. 12, Ed. by M. L. Wolfrom, Academic Press, New York (157) in the chapter *The Schardinger Dextrins* by Dexter French at p. 189–260; "Cyclodextrins and their Inclusion Complexes" by J. Szejtli, Akademiai Kiado, Budapest, Hungary (1982); I. Tabushi in Acc. Chem. Research, 1982, 15, p. 66–72; W. Sanger, Angewandte Chemie, 92, p. 343–361 (1981); A. P. Croft and R. A. Bartsch in Tetrahedron, 39, p. 1417–1474 (1983); German Offenlegungsschrift DE No. 3118218; German Offenlegungsschrift DE No. 3317064; EP-A-No. 94,157; EP-A-No. 149,197; EP-A-No. 197,571 which also mentions the antiviral agents of formula (I) below; U.S. Pat. No. 4,659,696; and U.S. Pat. No. 4,383,992.

Of particular utility in the invention are the β-cyclodextrin ethers, e.g. dimethyl-β-cyclodextrin as described in Drugs of the Future, Vol. 9, No. 8, p. 577–578 by M. Nogradi (1984) and polyethers, e.g. hydroxypropyl β-cyclodextrin, being examples. Such an alkyl ether may be a methyl ether with a degree of substitution of about 0.125 to 3, e.g. about 0.3 to 2. Such a hydroxypropyl cyclodextrin is formed from the reaction between β-cyclodextrin and propylene oxide and may have a MS value of about 0.125 to 10, e.g. about 0.3 to 3.

Of further particular utility are the β-and γ-cyclodextrin ethers described in EP-A-No. 149,197 and EP-A-No. 197,571, e.g. hydroxypropyl βand γ-cyclodextrin.

Antiviral agents to be used in the invention preferably comprise hydrophobic agents. Particular antivirals are synthetic non peptide agents of a molecular weight less than about 1000. Useful agents are those active against viruses such as those causing herpes or the common cold, such as picornaviruses, in particular, rhinoviruses, e.g. agents which are active in vitro or in vivo against viruses responsible for the common cold. In the invention, the molecules of the antiviral agent are surrounded, at least in part, by the cyclodextrin, i.e. the agent fits into the cyclodextrin cavity.

Particular agents include those of formula (I):

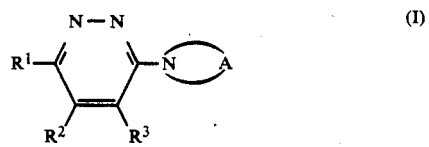

a pharmaceutically-acceptable acid-addition salt and/or a possible stereochemically isomeric form and/or a possible tautomeric form thereof wherein $R^1$ is hydrogen, halo, 1H-imidazol-1-yl, $C_{1-6}$alkyloxy, aryloxy, aryl$C_{1-6}$alkyloxy, $C_{1-6}$alkylthio, arylthio, hydroxy, mercapto, amino, $C_{1-6}$alkylsulfinyl, $C_{1-6}$alkylsulfonyl, cyano, $C_{1-6}$alkyloxycarbonyl, $C_{1-6}$alkylcarbonyl or $C_{1-6}$alkyl;

$R^2$ and $R^3$ are, each independently, hydrogen or $C_{1-6}$alkyl; or $R^2$ and $R^3$ combined may form a bivalent radical of formula —CH=CH—CH=CH—;

A is a bivalent radical of formula:

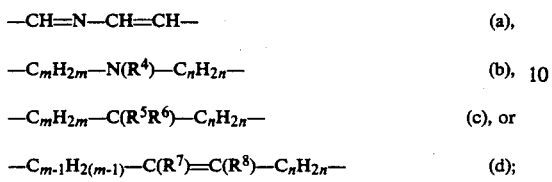

wherein one of the hydrogen atoms within the radical $C_mH_{2m}$, $C_{m-1}H_{2(m-1)}$ or $C_nH_{2n}$ may be replaced by $C_{1-6}$alkyl or aryl;

m and n are, each independently, integers of from 1 to 4 inclusive, the sum of m and n being 3, 4 or 5;

$R^4$ is hydrogen; $C_{1-6}$alkyl; aryl; thiazolyl; primidinyl; quinolinyl; $C_{1-6}$alkylcarbonyl; $C_{1-7}$alkoxycarbonyl; aryl$C_{1-6}$alkyl; diaryl$C_{1-6}$alkyl; phenyl being substituted with arylcarbonyl; pyridinyl, being optionally substituted with cyano or $C_{1-6}$alkyl; cyclohexyl or cyclohexenyl both being optionally substituted with up to two substituents independently selected from cyano and aryl;

$R^5$ is hydrogen, $C_{1-6}$alkyl; aryl; hydroxy; $C_{1-6}$alkyloxy; aryloxy; $C_{1-6}$alkyloxy being substituted with morpholine, pyrrolidine or piperidine; amino; ($C_{1-6}$alkyloxycarbonyl)amino; arylamino; (aryl)($C_{1-6}$alkyl)amino; (aryl$C_{1-6}$alkyl)amino; (aryl$C_{2-6}$alkenyl)amino; (aryl$C_{3-6}$ alkenyl)($C_{1-6}$alkyl)amino; or arylcarbonyloxy;

$R^6$ is hydrogen; aryl; $C_{1-6}$alkyl; ($C_{1-6}$alkylcarbonylamino)$C_{1-6}$alkyl, aryl$C_{1-6}$alkyl; arylcarbonyl$C_{1-6}$alkyl; aminocarbonyl; arylcarbonyl; arylaminocarbonyl; (aryl$C_{1-6}$alkyl)carbonyl; $C_{1-6}$alkyloxycarbonyl; indolyl; or pyridinyl;

$R^7$ and $R^8$ are, each independently, hydrogen $C_{1-6}$alkyl, aryl, aryl$C_{1-6}$alkyl or pyridinyl;

wherein aryl is phenyl, being optionally substituted with up to 3 substituents, each independently selected from halo, $C_{1-6}$alkyl, trifluoromethyl, nitro, amino, $C_{1-6}$alkyloxy, hydroxy and $C_{1-6}$alkyloxycarbonyl; thienyl; and naphtalenyl;

such compounds of formula (I) being prepared as described in European Patent Application No. 156,433 published Oct. 2, 1985 which corresponds to U.S. Ser. No. 702,772. Particular agents within this group include the following:

3-chloro-6-[3,6-dihydro-4-(3-methylphenyl)-1(2H)-pyridinyl]pyridazine;

3-chloro-6-[3-[3-(trifluoromethyl)phenyl]-1-pyrrolidinyl]pyridazine;

3-methyl-6-[3-[3-(trifluoromethyl)phenyl]-1-pyrrolidinyl]pyridazine;

3-iodo-6-[3-[3-(trifluoromethyl)phenyl]-1-pyrrolidinyl]pyridazine;

3-bromo-6-[3-[3-(trifluoromethyl)phenyl]-1-pyrrolidinyl]pyridazine;

3-[3,6-dihydro-4-(3-methylphenyl)-1(2H)-pyridinyl]-6-methoxypyridazine;

3-methoxy-6-[4-(3-methylphenyl)-1-piperazinyl]pyridazine;

3-bromo-6-[4-(3-methylphenyl)-1-piperazinyl]pyridazine.

As used in the above definitions, $C_{1-6}$alkyl is as defined hereinabove; $C_{3-6}$alkenyl defines straight and branch chained hydrocarbon radicals having one double bond, and having from 3 to 6 carbon atoms, for example, 2-propenyl, 2-butenyl, 3-butenyl and the like; the carbon atom of said $C_{3-6}$alkenyl being linked to a heteroatom being preferably saturated.

A second group of antiviral agents for the invention are those of the following formula (II):

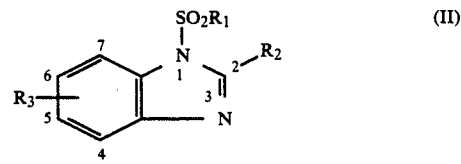

wherein $R_1$ is $C_1$–$C_5$ alkyl, $C_3$–$C_7$ cycloalkyl, phenyl, furyl, thienyl, thiazol-2-yl, 2-acetamido-4-methylthiazol-5-yl, 1,3,4-thiadiazol-2-yl, 2-methyl-1,3,4-thiadiazol-5-yl, 2-methylamino-1,3,4-thiadiazol-5-yl or $R_4R_5N$—, wherein $R_4$ and $R_5$ are independently $C_1$–$C_3$ alkyl or $R_4$ and $R_5$, when taken together with the nitrogen atom to which they are attached, are pyrrolidino, piperidino or morpholino;

$R_2$ is amino, formamido, acetamido, propionamido or butyramido;

$R_3$ is hydroxy, $C_2$–$C_8$ alkanoyloxy, phenylacetoxy, $\alpha$-$C_1$–$C_7$ alkyl-$\alpha$-hydroxybenzyl or benzoyloxy; or 1,3-dithiolan-2-yl, 1,3-dithian-2-yl, tetrazol-5-yl, 1-($C_1$-$C_4$alkyl)tetrazol-5-yl, 1,3,4-oxadiazol-2-yl, or 2-($C_1$-$C_4$alkyl)oxadiazol-5-yl; or

wherein $R_4$ is hydrogen, $C_1$–$C_7$alkyl, $C_3$–$C_7$cycloalkyl, ($C_3$–$C_7$ cycloalkyl)methyl, 1-($C_3$–$C_7$ cycloalkyl)ethyl, benzyl, phenyl or phenyl substituted by $C_1$–$C_4$ alkyl, $C_1$–$C_4$ alkoxy, chloro, bromo, iodo, nitro or trifluoromethyl; or Z=C($R_4$)—, wherein Z is hydroxyimino, $C_1$–$C_4$ alkoxyimino, $C_1$–$C_4$ acyloxyimino, benzyloxyimino, benzoyloxyimino, hydrazono, thiocarbamylhydrazono, carboxymethoxyimino, methoxycarbonylhydrazono, ethoxycarbonylhydrazono, carbamylhydrazono, $C_1$–$C_4$ alkoxycarbonylethylcarbonyloxyimino, benzyloxycarbonylaminomethylcarbonyloxyimino, p-nitrobenzyloxycarbonylethylcarbonyloxyimino, phthalimidomethylcarbonyloxyimino, 2-(2-benzyloxycarbonyl-5-oxoisoxazolidin-4-yl)ethylcarbonyloxyimino or $C_1$–$C_7$ alkylidene; and $R_3$ is at the 5 or 6 position, such compounds of formula (II) being prepared as described in U.S. Pat. No. 4,118,742. A particular agent of this group is enviroxime which is 2-amino-1-(isopropyl sulphonyl)-6-benzimidazole phenyl ketone oxime.

As used in the foregoing definitions $C_{1-5}$alkyl is as $C_{1-6}$alkyl defined hereinabove, hexyl and its isomers being excluded; $C_{3-7}$cycloalkyl refers to the saturated alicyclic rings having from 3 to 7 carbon atoms; $C_{1-3}$alkyl defines methyl, ethyl, propyl and 2-propyl; $C_{2-8}$alkanoyl refers to the straight chain aliphatic acyl radicals of 2 to 8 carbon atoms and the branched aliphatic aryl radicals of four to five carbon atoms such as acetyl, propionyl, butyryl, 2-methylproprionyl, pentanoyl, hexanoyl, heptanoyl, octanoyl, and the like; $C_{1-7}$alkyl comprises $C_{1-6}$alkyl and heptyl and the heptyl isomers. $C_{1-4}$alkyl comprises $C_{1-3}$alkyl and butyl and the butyl isomers; $C_{1-7}$alkylidene defines bivalent saturated hydrocarbon radicals, straight or branch chained, having from 1 to 7 carbon atoms.

A third group of antiviral agents for the invention are those of the following formula (III):

$$\text{(III)}$$

or, where appropriate, a pharmaceutically-acceptable salt thereof, wherein $R^1$ and $R^2$ represent halogen atoms or nitro, cyano, trifluoromethyl, $C_{1-6}$alkyl, lower alkoxyl, $C_{1-6}$alkylamino, amino or hydroxyl groups. Chloro, nitro, cyano and hydroxyl groups are preferred and chlorine is the most preferred substituent. In formula (III), $R^1$ may represent hydrogen or up to 4 substituents and $R^2$ may represent hydrogen or up to 5 substituents. It is preferred that $R^1$ and $R^2$ each represent up to 2 substituents and most preferably $R^1$ and $R^2$ each represent one substituent. Preferably, the compound has substituents $R^1$ at the 6 or 7 positions and/or $R^2$ at the 2',3',4',5' or 6' positions, the 6 and 4' positions being particularly preferred. Compounds of formula (V) may be prepared as described in U.S. Pat. No. 4,461,907 with a particular compound being 4'6-dichloroflavan, also known as dichloroflavan.

A fourth group of antiviral agents for the invention are those of the following formula (IV):

$$\text{(IV)}$$

wherein
$R^1$ represents hydroxy, acyloxy derived from an aliphatic acid having 2–18 carbon atoms or a heterocyclic carboxylic acid containing nitrogen atom(s), lower alkoxycarbonyloxy, aminoacyloxy or carboxyalkanoyloxy;
$R^2$ represents lower alkoxy;
$R^3$ represents hydrogen or lower alkoxy; and
$R^4$ represents phenyl which may be substituted by one or more substituents selected from the group consisting of $C_{1-6}$alkyl, lower alkoxy, benzyloxy, allyloxy, alkylthio, dialkylamino, amino, cyano, hydroxy, halo and alkylenedioxy; or pyridyl, furyl, thienyl or pyrrolyl which may be substituted by $C_{1-6}$alkyl, such compounds being prepared as described in U.S. Pat. No. 4,605,674. A particular species of such group is 4'-ethoxy-2'-hydroxy-4,6'-dimethoxychalcone, also known as Ro 09-0410. In the above definition lower alkyloxycarbonyloxy may contain up to 7 carbon atoms; aminoacyloxy can be derived from an aliphatic aminoacid; carboxyalkanoyloxy can be derived from a dicarboxylic acid of 2 to 8 carbon atoms, for example; lower alkyloxy contains 1 to 4 carbon atoms.

A fifth group of antiviral agents for the invention are those of the following formula (V):

$$\text{(V)}$$

wherein
R is a straight or branched saturated hydrocarbon chain having from 12 to 16 carbon atoms or a straight or branched unsaturated hydrocarbon chain having from 12 to 16 carbon atoms and from 1 to 4 double bond;

such compounds being prepared as described in U.S. Pat. No. 4,602,099. A species of such group of compounds is 1-(5-tetradecyloxy-2-furanyl)ethanone, also known as RMI-15,731.

A sixth group of antiviral agents for the invention are those of the following formula (VI-a) and (VI-b):

$$\text{(VI-a)}$$

$$\text{(VI-b)}$$

wherein:
R, $R_1$, $R_2$, $R_3$ and $R_4$ are each hydrogen or alkyl of 1 to 3 carbon atoms optionally substituted by hydroxy, lower alkanoyloxy, lower alkoxy, chloro, or N=Z, wherein N=Z is amino, lower alkanoylamino, lower alkylamino, di-lower alkylamino, 1-pyrrolidinyl, 1-piperidinyl or 4-morpholinyl; with the proviso that R is other than hydrogen;
$R_5$ is hydrogen, lower-alkyl, halogen, nitro, loweralkoxy, lower-alkylthio or trifluoromethyl;
$R_6$ is alkyl of 1 to 3 carbon atoms;
X is 0 or a single bond; and
n is an integer from 3 to 9;
and the pharmaceutically acceptable acid-addition salts thereof, such compounds being prepared as described in European Patent Application No. 137,242 published Apr. 17, 1985. Particular species of such class of compounds are 5-[7-[4-(4,5-dihydro-2-isoxazole)phenoxy]-heptyl]-3-methylisoxazole, also known as WIN 51,711; 5-[5-[2-bromo-4-(4,5-dihydro-2-oxazolyl)phenoxy]-phenyl]-3-methylisoxazole and 5-[5-[2-nitro-4-(4,5-dihydro-2-oxazolyl)phenoxy]phenyl]-3-methylisoxazole.

Other groups of antiviral compounds for the invention are:

(7) The oxazoles and oxazines of European Patent Application No. 207,454 published Jan. 7, 1987, e.g. 5-(5-(2,6-dichloro-4-(4,5-dihydro-2-oxazolyl)phenoxy)pentyl-3-methylisoxazole;

(8) The 5-(4-heterocyclic)-phenoxy)alkyl isoxazole and furan compounds of European Patent Application No.

207,453 published Jan. 7, 1987, e.g. 5-(5-(2,6-dichloro-4-(2-furanyl)phenoxy)pentyl)-3-methylisoxazole and 5-(5-(2,6-dichloro-4-(2-pyridyl)phenoxy)pentyl)-3-methylisoxazole;

(9) The isoxazoles of U.S. Pat. No. 4,451,476, e.g. 5-(7-(2-chloro-4-methoxyphenoxy)heptyl)-3-methylisoxazole (WIN-49321);

(10) The 3-alkoxy-5,7-dihydroxy flavone derivatives of European Patent Application No. 19,081 published Nov. 26, 1980, e.g. 4',5-dihydroxy-3,3',7-trimethoxyflavone (RO 09-0179), 4',5-diacetyloxy-3,3',7-trimethoxyflavone (RO 09-0298);

(11) The substituted phenyl (thio)ketone benzo-oxamidines of European Patent Application No. 51,819 published May 19, 1982, e.g. 4-ethoxy-2-hydroxy-6-methoxy-N-(4-methoxybenzyl)benzamide (RO 09-0535) and 1-(2-hydroxy-4,6-dimethoxyphenyl)-3-(4-methoxyphenyl)-1-propanone (RO 09-0487);

(12) The 2-piperazinyl-1,3-thiazole-4-carboxylic acids of European Patent Application No. 187,618 published July 16, 1986, e.g. 2-[4-(2,5-dimethylbenzyl)-1-piperazinyl]-1,3-thiazole-4-carboxylic acid;

(13) The 2-pyridyl amino methylbenzimidazoles of European Patent Application No. 209,106 published January 21, 1987, e.g. 2-(4-pyridylaminomethyl)-benzimidazole;

(14) The trans-6-propenyl benzimidazoles of U.S. Pat. No. 4,424,362 issued Jan. 3, 1984 which is incorporated by reference, e.g. (E)-2-amino-1-isopropylsulfonyl-6-(1-phenyl-1-propenyl)benzimidazole (Ly 127,123; Enviradene);

(15) The 2-phenoxy or phenylthio substituted benzonitriles of U.S. Pat. No. 4,254,144 issued Mar. 3, 1981 incorporated by reference, e.g. (2-(3,4-di-chlorophenoxy)-5-nitrobenzonitrile (MDL 26,014 or MDL 860);

(16) The 2-phenylpyrano[2,3-b]pyridines of U.S. Pat. No. 4,588,733 issued May 13, 1986 incorporated by reference, e.g. 6-methylsulfonyl-2-(3,4-dichlorophenyl)-3,4-dihydro-2H-pyrano[2,3-b]pyridine and 6-chloro-2-(4-chlorophenyl)-3,4-dihydro-2H-pyrano[2,3-b]pyridine;

(17) The 2,5-bis(alkyl-thio or -sulphonyl)pyridines of U.S. Pat. No. 4,616,087 issued Oct. 7, 1986 incorporated by reference, e.g. 2-(3,4-dihalophenoxy)-5-(methylsulfonyl)pyridine (MDL 055);

(18) The methenopentalene compounds of EP-A-No. 2,896, e.g. octahydro-α-methyl-1,2,4-methenopentalene-5-methanamine;

(19) The isoxazole derivatives of EP-A-No. 211,157, e.g. 5-[7-[5-(4,5-dihydro-2-oxazolyl)-2-thienyl]oxyheptyl]-3-methylisoxazol, 5-[7-[5-(4,5-dihydro-2-oxazolyl)-4-thienyl]oxyheptyl]-3-methylisoxazol.

To prepare the pharmaceutical compositions of the invention, the selected antiviral agent (or agents) is deposited within the cyclodextrin molecule itself, such process being known in the art for other active agents. In the final composition, the molar ratio of cyclodextrin:antiviral agent is from about 1:1 to about 5:1, in particular, about 1:1 to about 2:1. Thus, in general, the composition will be prepared by dissolving the cyclodextrin in water and adding the antiviral compound to this solution, preferably under vigorous stirring and preferably at a temperature in the range of 10° to 50° C., in particular in the range of 15° to 30° C., and preferably at room temperature.

In the final composition, the cyclodextrin will comprise about 2.5 to 40% by weight, in particular about 2.5 to 25%, more in particular 5 to 25%, or 5 to 20%, for example about 10%, with the remainder being water, preservative, the active ingredient and any excipients.

In particular, the pharmaceutical composition may consist only of water, cyclodextrin and the antiviral agents without the need for co-solvents such as ethanol or surfactants.

Application of the pharmaceutical composition of the invention may be by aerosol, e.g. with a propellant such as nitrogen, carbon dioxide, a freon, or without a propellant such as a pump spray, drops, or a semisolid such as a thickened composition which can be applied by a swab. In particular applications, semisolid compositions such as salves, creams, gellies, ointments and the like will conveniently be used.

For liquid preparations, any of the usual pharmaceutical media may be added, such as, for example, glycols, oils, alcohols and the like, however in concentrations below the level of irritation. In order to stabilize the formulations the pH may be increased or decreased or stabilized by adding appropriate acids, bases or buffer systems, e.g. citrate, phosphate buffers. Further additives may comprise substances to make the formulations isotonical, e.g. sodium chloride, mannitol, glucose and the like. It is further recommendable to add a preservative to the formulations such as, for example, a mercury salt or complex salt, e.g. phenyl mercuriacetate, nitrate, chloride or borate, phenylethyl alcohol, ethanol, propylene glycol and the like. Suitable thickeners for obtaining the above-mentioned thickened compositions comprise polyvinyl alcohols, hydroxypropyl methyl celluloses, hydroxyethyl celluloses, methylcelluloses, polyvinyl pyrrolidone, acrylic acid polymers and the like.

Depending on the type of virus which is to be controlled, compositions within the scope of the invention can be applied in the vagina, nose, mouth, eyes, lungs or within the cheeks so as to control viruses which have not entered the blood stream of the patient, e.g. viruses which are located in mucous membranes of the body. The pharmaceutical compositions of the invention are particularly useful on those infection sites where the natural defense mechanisms prevent the delivery of antiviral agents during sustained periods due to an effective elimination of the active compound from the site of infection. Such elimination may be due to clearance by ciliary movement or secretion, or by absorption.

As part of the pharmaceutical composition, one may also include the same or a different active antiviral in a different delivery carrier so as to provide a different profile of activity, e.g. a wide range of time during which the composition shows activity or a supplement to bolster a low level at a particular point in the release schedule of the cyclodextrin.

A. COMPOSITION EXAMPLES

Example 1

To a solution of 0.1 g of hydroxypropyl β-cyclodextrin (MS=0.43) in 0.7 ml of distilled water are added 730 μg of a 0.1N hydrochloric acid solution and 2.5 mg of 3-methoxy-6-[4-(3-methylphenyl)-1-piperazinyl]-pyridazine. After stirring for 10 minutes at room temperature, the pH of the thus obtained solution is adjusted to pH 5.5 by adding a 0.1N sodium hydroxide solution. Then there are added successively 4 mg of sodium chloride and 0.15 mg of phenyl mercuri acetate and the whole is stirred to produce a complete solution. Distilled water is then added to a volume of 1.0 ml. The whole is filled in a glass bottle closed with a mechanical pump spray delivering 0.1 ml per puff upon administration.

Example 2

To a solution of 0.1 g of dimethyl β-cyclodextrin in 0.7 ml of distilled water are added 600 μg of a 0.1N hydrochloric acid solution and 2 mg of 3-chloro-6-[3-[3-(trifluoromethyl)phenyl]-1-pyrrolidinyl]pyridazine. After stirring for 10 minutes at room temperature, 10 mg of polyvinylalcohol is dissolved in the mixture and the pH of the thus obtained solution is adjusted to pH 5.5 by adding a 0.1N sodium hydroxide solution. Then there are added successively 4 mg of sodium chloride and 2 mg of phenylethyl alcohol and the whole is stirred to produce a complete solution. Distilled water is added to produce a volume of 1.0 ml which is filled in a glass bottle closed with a mechanical pump spray delivering 0.1 ml per puff upon administration.

Example 3

To a stirred and warmed (45°-50° C.) solution of 100 mg of methyl β-cyclodextrin in 8.0 ml of water is added 2.5 mg of WIN 51,711 and stirring is continued until complete solution is achieved. Then there are added successively 6 mg of sodium chloride and 0.015 mg of phenyl mercuriacetate. Upon complete solution, distilled water is added to produce a volume of 10 ml is reached. The solution is filled into a glass bottle with a mechanical spray pump.

Example 4

To a stirred and warmed (45°-50° C.) solution of 200 mg of methylhydroxypropyl β-cyclodextrin (a mixed ether having both methyl and hydroxypropyl moieties) in 8.0 ml of water is added 1.0 mg of RMI 15731 and stirring is continued until a complete solution is produced. Then there are added successively 3 mg of sodium chloride and 0.015 mg of phenyl mercuriacetate. Upon complete solution, distilled water is added until a volume of 10 ml is reached. The solution is filled into a glass bottle with a mechanical spray pump.

Example 5

To a stirred and warmed (45°-50° C.) solution of 150 mg of hydroxypropyl β-cyclodextrin in 8.0 ml of water is added 0.5 mg of enviroxime and stirring is continued until a complete solution is produced. Then there are added successively 5.0 mg of sodium chloride and 0.015 mg of phenyl mercuri acetate. Upon complete solution, distilled water is added until a volume of 10 ml is reached. The solution is filled into a glass bottle with a mechanical spray pump.

Example 6

To a stirred and warmed (45°-50° C.) solution of 125 mg of dimethyl β-cyclodextrin and 1.0 ml of a citrate phosphate buffer (pH=7), previously prepared started from 37 mg of citric acid monohydrate and 293.17 mg disodium monohydrogen phosphate dihydrate in 8.0 ml of distilled water are added 1.0 mg of dichloroflavan. Stirring is continued until a complete solution is achieved. Then there are added successively 50 mg of glucose and 0.015 mg of phenyl mercuri acetate. Upon complete solution, distilled water is added to a volume of 10 ml. The solution is filled into a glass bottle with a mechanical spray pump.

Example 7

To a stirred and warmed (45°-50° C.) solution of 150 mg of hydroxyethyl β-cyclodextrin in 8.0 ml of distilled water is added 0.75 mg of 3-iodo-6-[3-[3-(trifluoromethyl)phenyl]-1-pyrrolidinyl]pyridazine and stirring is continued until a complete solution is achieved. Then there are added successively 5 mg of sodium chloride and 0.015 mg of phenyl mercuri acetate. Upon complete solution, distilled water is added to yield a volume of 10 ml. The solution is filled into a glass bottle with a mechanical spray pump.

Example 8

To a stirred and warmed (45°-50° C.) solution of 125 mg of methyl β-cyclodextrin in 8.0 ml of distilled water are added 0.05 mg of 3-chloro-6-[3,6-dihydro-4-(3-methylphenyl)-1(2H)-pyridinyl]pyridazine and stirring is continued to give a solution. Then there are added successively 7 mg of sodium chloride and 0.015 mg of phenyl mercuri acetate. Upon complete solution, distilled water is added to yield a volume of 10 ml. The solution is filled into a glass bottle with a mechanical spray pump.

Example 9

To a stirred and warmed (45°-50° C.) solution of 100 mg of hydroxypropyl β-cyclodextrin and 1.0 ml of a citrate phosphate buffer (pH=5), previously prepared from 37 mg of citric acid monohydrate, 293.17 mg disodium monohydrogen phosphate dihydrate, 50 mg of ethanol and 50 mg of propyleneglycol in 8.0 ml of distilled water is added 7.5 mg of 3-methyl-6-[3-[3-(trifluoromethyl)phenyl]-1-pyrrolidinyl]pyridazine and stirring is continued until a complete solution is achieved. Then there are added successively 50 mg of glucose and 0.015 mg of phenyl mercuri acetate. Upon complete solution, distilled water is added to increase the volume to 10 ml. The solution is filled into a glass bottle with a mechanical spray pump.

Example 10

To a stirred and warmed (45°-50° C.) solution of 200 mg of α-cyclodextrin in 8.0 ml of distilled water is added 0.01 mg of 3-chloro-6-[4-[3-[4-(4,5-dihydro-4,4-dimethyl-2-oxazolyl)phenoxy]propyl]-1-piperidinyl]-pyridazine and stirring is continued until a complete solution is achieved. Then there are added successively 4 mg of sodium chloride and 0.015 mg of phenyl mercuri acetate. Upon complete solution, distilled water is added to a volume of 10 ml is reached. The solution is filled into a glass bottle with a mechanical spray pump.

B. PHARMACOLOGICAL EXAMPLES

Clinical Trial

Healthy volunteers of either sex aged between 18 and 50 years were recruited and housed in isolation in groups of two or three according to normal practice. All volunteers completed a questionnaire to assess their introversion/extroversion and certain obsessional factors as these have been shown to influence the outcome of virus challenge. The virus challenge was a bacteriologically sterile nasal wash pool containing RV9 and propagated by serial intranasal passage in volunteers.

Study Design - Initial blood samples were collected from every volunteer on arrival for hematological and biochemical examination. After a two-day quarantine period, the volunteers were divided into two groups matched for age and sex. One group received drug (the composition of Example 1), two sprays to each nostril, six times a day at 8 am, 11 am, 2 pm, 5 pm, 8 pm and 10:30 pm. The other group was given placebo at the same quantity and frequency. Medication continued for four days and one dose so that the total quantity of drug given was 25 mg. One hour after the eighth dose of medication volunteers were challenged, intranasally, with an estimated 100 $TCID_{50}$ of RV9 except for a few who were given saline. Each volunteer was assessed daily by a clinician who was unaware of the medication and challenge they had received. A score was allotted according to the signs and symptoms present and, in addition, the amount of nasal secretion produced each day was weighted. At the end of the trial, the clinical observer assessed each volunteer as having suffered no cold, doubtful cold (not significant), or a significant cold of a mild, moderate or severe nature. Blood samples for repeat hematological and biochemical tests and drug assay were collected within 10 to 20 minutes of final medication. An aliquot of all nasal washings was stored for drug assay and the time of collection and that of all medication was recorded. In an initial study, the virus challenge was omitted in order that the tolerance of the volunteers to the drug and vehicle could be assessed.

Virological Procedures - Nasal washings were collected from each volunteer prior to and daily from day 2 to day 6 after inoculation, mixed with an equal volume of nutrient broth and stored at $-70°$ C. Virus isolation was not undertaken as no completely satisfactory method for dissociating drug from virus in the nasal washings has been devised. Part of the nasal washing was stored at $-20°$ C. for drug assay. Serum neutralizing antibody titres were assayed by a micro-neutralization test on the initial blood sample and a further sample collected approximately 3/52 after the challenge. A four-fold or greater rise in concentration was taken as evidence of infection.

Statistical Analysis - Differences in the frequency of colds and antibody rises between the drug and placebo treated groups were tests for significance using the Chi-squared test with Yates correction. Clinical score and nasal secretion weight data were tested by rank analysis of variance with each variable divided into three strata according to the pre-challenge serum neutralizing titre of each volunteer ($<1:2$; 1:2 to 1:8 and $>1:8$).

Tolerance Study - Ten volunteers, five drug and five placebo, took part in the tolerance study. A further six volunteers in the prophylactic trial, three drug and three placebo, received saline instead of virus. None of these sixteen volunteers were diagnosed as suffering a cold or reaction of any degree. The mean total score for the eight volunteers receiving drug was 0 and that for the eight placebo recipients was 0.375.

Prophylaxis Study - During the course of three prophylaxis trials, 62 volunteers participated. One was excluded because of abnormal results of hematological tests, six were challenged with saline and the remaining 55 were given virus. Of these 55 volunteers, 28 received drug and 27 placebo and the two groups were well balanced for age, sex, pre-trial antibody titres and psychological scores. Six colds, all mild, occurred in the drug group and six, one moderate and five mild, in the placebo group. The mean total clinical score for those receiving drug was 3.36 and that for the placebo group 4.94. Fifteen of the convalescent sera received from 26 volunteers in each group showed a significant rise in antibody concentration to the challenge virus.

As shown in Tables I and II, the first three days after virus challenge (days 5, 6 and 7), both mean clinical score and mean nasal secretion weight were higher in the placebo group than in the drug group and these differences reach statistical significance, $0.05>p>0.01$, for mean clinical score on day 5 and for mean nasal secretion weight on day 7. On days 8 and 9, the mean clinical score was higher, although not significantly so, in the drug group than the placebo group and the mean nasal secretion weight was markedly increased in the drug group and approximated to but did not exceed that of the placebo group.

TABLE I

| MEAN NASAL SECRETION WEIGHT (g) | | |
| --- | --- | --- |
| day | drug group | placebo group |
| 1 | 0.09 | 0.43 |
| 2 | 0.35 | 0.24 |
| 3 | 0.10 | 0.37 |
| 4 | 0.18 | 0.28 |
| 5 | 0.20 | 1.33 |
| 6 | 0.17 | 2.18 |
| 7 | 0.21 | 1.41 |
| 8 | 1.19 | 1.77 |
| 9 | 1.58 | 1.65 |

TABLE II

| MEAN CLINICAL SCORE | | |
| --- | --- | --- |
| day | drug group | placebo group |
| 1 | 0 | 0 |
| 2 | 0 | 0 |
| 3 | 0 | 0 |
| 4 | 0 | 0.04 |
| 5 | 0.16 | 0.83 |
| 6 | 0.29 | 1.41 |
| 7 | 0.23 | 1.07 |
| 8 | 1.39 | 0.98 |
| 9 | 1.29 | 0.59 |

Discussion of Results - The drug was well tolerated by all volunteers with no evidence of local irritation and no significant change in the results of hemotalogical and biochemical tests performed before and after medication. The gross analysis of the results suggests that the active ingredient had little effect on infection with RV9 as there were as many colds of similar severity in the drug as in the placebo group and the same proportion of volunteers seroconverted in the two groups. However, on a daily basis, it is obvious that the colds were occurring some three days later in the drug group compared with the placebo group. Furthermore, the onset of colds in the drug group commenced 24 hours after medication ceased indicating that, with this regime, the presence of drug is inhibiting the development of the rhinovirus infection which then progresses when drug is withdrawn. The later onset of colds in the drug group could well account for the lower mean total clinical score (3.36) compared with that of the placebo group (4.92). That infection had occurred in those volunteers receiving drug at the normal time following challenge is suggested by the slight increase in both mean clinical score and mean nasal secretion weight on days 5, 6 and 7 compared with the four previous days.

This trial has clearly shown that intranasal administration with the pharmaceutical composition of the invention given six times a day will present clinical signs of infection of volunteers with RV9 for the period of drug (or formulation) administration. Clinical illness develops when such medication is discontinued 3 days after challenge.

What is claimed is:

1. A pharmaceutical composition for treating a rhino viral infection in a mammal which comprises a cyclodextrin and an anti-rhinoviral agent, with the proviso that if the cyclodextrin is a γ-cyclodextrin ether or mixed ether, wherein the ether substituents are $C_{1-6}$alkyl, hydroxy$C_{1-6}$alkyl, carboxy$C_{1-6}$alkyl or ($C_{1-6}$alkyloxycarbonyl)$C_{1-6}$alkyl, then said agent is not of the following formula:

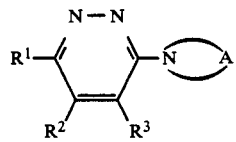

a pharmaceutically-acceptable acid-addition salt and/or a stereochemically isomeric form and/or a possible tautomeric form thereof, wherein $R^1$ is a member selected from the group consisting of hydrogen, halo, 1H-imidazol-1-yl, lower alkyloxy, aryloxy, aryllower alkyloxy, lower alkylthio, arylthio, hydroxy, mercapto, amino, lower alkylsulfinyl, lower alkylsulfonyl, cyano, lower alkyloxycarbonyl, lower alkylcarbonyl, and lower alkyl;

$R^2$ and $R^3$ are, each independently, members selected from the group consisting of hydrogen and lower alkyl, or $R^2$ and $R^3$ combined may form a bivalent radical of formula —CH=CH—CH=CH—;

A is a bivalent radical of formula:

—CH=N—CH=CH— (a),

—CH=N—CH=CH—, (a)

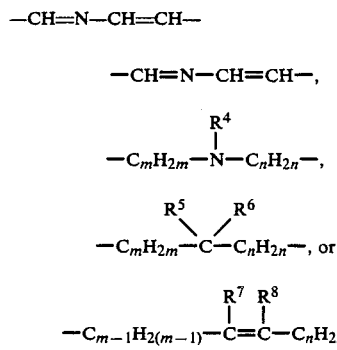

wherein one of the hydrogen atoms within the radical $C_mH_{2m}$, $C_{m-1}H_{2(m-1)}$ or $C_nH_{2n}$ may be replaced by lower alkyl or aryl;

m and n are, each independently, integers of from 1 to 4 inclusive, the sum of m and n being 3, 4 or 5;

$R^4$ is a member selected from the group consisting of hydrogen; lower alkyl; aryl; thiazolyl; pyrimidinyl; quinolinyl; lower alkylcarbonyl; lower alkyloxycarbonyl; aryllower alkyl; diaryllower alkyl; phenyl being substituted with arylcarbonyl; pyridinyl which may be substituted with cyano or lower alkyl; cyclohenyl and cyclohexenyl both of which may be substituted with up to two substituents independently selected from the group consisting of cyano and aryl;

$R^5$ is hydrogen; lower alkyl; aryl; hydroxy; lower alkyloxy; aryloxy; lower alkyloxy being substituted with morpholine, pyrrolidine or piperidine; amino; (lower alkyloxycarbonyl)amino; arylamino; (aryl)(lower alkyl)amino; (aryllower alkyl)amino; (aryllower alkenyl)amino; (aryllower alkenyl)(lower alkyl)amino; arylcarbonyloxy;

$R^6$ is hydrogen; aryl; lower alkyl; (lower alkylcarbonyl amino)lower alkyl, aryllower alkyl; arylcarbonyllower alkyl; aminocarbonyl; arylcarbonyl; arylaminocarbonyl; (aryllower alkyl)carbonyl, lower alkyloxycarbonyl; indolyl; or pyridinyl;

$R^7$ and $R^8$ are, each independently, members selected from the group consisting of hydrogen, lower alkyl, aryl, aryllower alkyl and pyridinyl;

wherein aryl is phenyl which may be substituted with up to 3 substituents, each independently selected from the group consisting of halo, lower alkyl, trifluoromethyl, nitro, amino, lower alkyloxy, hydroxy and lower alkyloxycarbonyl; thienyl; and naphthalenyl; lower alkyl comprises straight and branch chained saturated hydrocarbon radicals having from 1 to 6 carbon atoms; lower alkenyl comprises alkenyl radicals having from 2 to 6 carbon atoms.

2. A composition according to claim 1 wherein the anti-rhino viral agent is a hydrophobic nonpeptide agent.

3. A composition according to claim 2 wherein the cyclodextrin is a β- or γ-cyclodextrin.

4. A composition according to claim 3 wherein the cyclodextrin is a β-or γ-cyclodextrin ether or mixed ether wherein the ether substituents are $C_{1-6}$alkyl, hydroxy$C_{1-6}$alkyl, carboxy$C_{1-6}$alkyl, or ($C_{1-6}$alkyloxycarbonyl)$C_{1-6}$alkyl.

5. A composition according to claim 4 wherein the ether substituents are $C_{1-3}$alkyl, hydroxy$C_{2-4}$alkyl or carboxy$C_{1-2}$alkyl.

6. A composition according to claim 5 wherein the ether substituents are methyl, ethyl, hydroxyethyl, hydroxypropyl, hydroxybutyl, carboxymethyl or carboxyethyl.

7. A composition according to claim 4 wherein the DS is in the range of 0.125 to 3 and the MS is in the range of 0.125 to 10.

8. A composition according to claim 7 wherein the DS is in the range of 0.3 to 2 and the MS is in the range of 0.3 to 3.

9. A composition according to claim 1 wherein the molar ratio of cyclodextrin:anti-rhinoviral agent in said composition is in the range from 1:1 to 5:1.

10. A composition according to claim 9 wherein the molar ratio of cyclodextrin:anti-rhinoviral agent in said composition is in the range from 1:1 to 2:1.

11. A composition according to claim 1 wherein the said cyclodextrin is present in said composition in an amount of about 5 to 15% weight per cent.

12. A composition according to claim 1 which is an aerosol.

13. A composition according to claim 2 wherein the said anti-rhinoviral agent is a compound having the formula

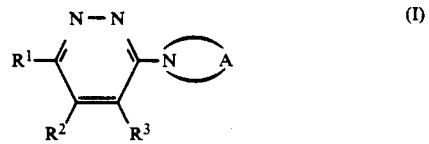

a pharmaceutically-acceptable acid-addition salt and/or a stereochemically isomeric form and/or a possible tautomeric form thereof wherein $R^1$ is hydrogen, halo, 1H-imidazol-1-yl, $C_{1-6}$alkyloxy, aryloxy, aryl$C_{1-6}$alkyloxy, $C_{1-6}$alkylthio, arylthio, hydroxy, mercapto, amino, $C_{1-6}$alkylsulfinyl, $C_{1-6}$alkylsulfonyl, cyano, $C_{1-6}$alkyloxycarbony, $C_{1-6}$alkylcarbonyl or $C_{1-6}$alkyl;

$R^2$ and $R^3$ are, each independently, hydrogen or $C_{1-6}$alkyl; or $R^2$ and $R^3$ combined may form a bivalent radical of formula —CH=CH—CH=CH—;

A is a bivalent radical of formula:

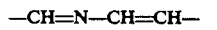  (a),

  (b),

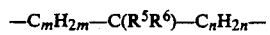  (c), or

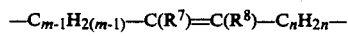  (d);

wherein one of the hydrogen atoms within the radical $C_mH_{2m}$, $C_{m-1}H_{2(m-1)}$ or $C_nH_{2n}$ may be replaced by $C_{1-6}$alkyl or aryl;

m and n are, each independently, integers of from 1 to 4 inclusive, the sum of m and n being 3, 4 or 5;

$R^4$ is hydrogen; $C_{1-6}$alkyl; aryl; thiazolyl; pyrimidinyl; quinolinyl; $C_{1-6}$alkylcarbonyl; $C_{1-6}$alkyloxycarbonyl; aryl$C_{1-6}$alkyl; diaryl$C_{1-6}$alkyl; phenyl being substituted with arylcarbonyl; pyridinyl, which may be substituted with cyano or $C_{1-6}$alkyl; cyclohexyl or cyclohexenyl both of which may be substituted with up to two substituents independently selected from cyano and aryl;

$R^5$ is hydrogen; $C_{1-6}$alkyl; aryl; hydroxy; $C_{1-6}$alkyloxy; aryloxy; $C_{1-6}$alkyloxy being substituted with morpholine, pyrrolidine or piperidine; amino; ($C_{1-6}$alkyloxycarbonyl)amino; arylamino; (aryl)($C_{1-6}$alkyl)amino; (aryl$C_{1-6}$alkyl)amino; (aryl$C_{2-6}$alkenyl)amino; (aryl$C_{3-6}$alkenyl)($C_{1-6}$alkyl)amino; or arylcarbonyloxy;

$R^6$ is hydrogen; aryl; $C_{1-6}$alkyl; ($C_{1-6}$alkylcarbonylamino)$C_{1-6}$alkyl, aryl$C_{1-6}$alkyl; arylcarbonyl$C_{1-6}$alkyl; aminocarbonyl; arylcarbonyl; arylaminocarbonyl; (aryl$C_{1-6}$alkyl)carbonyl; $C_{1-6}$alkyloxycarbonyl; indolyl; or pyridinyl;

$R^7$ and $R^8$ are, each independently, hydrogen, $C_{1-6}$alkyl, aryl, aryl$C_{1-6}$alkyl or pyridinyl;

wherein aryl is phenyl which may be substituted with up to 3 substituents, each independently selected from halo, $C_{1-6}$alkyl, trifluoromethyl, nitro, amino, $C_{1-6}$alkyloxy, hydroxy and $C_{1-6}$alkyloxycarbonyl; thienyl; and naphthalenyl.

14. A composition according to claim 13 wherein the said anti-rhinoviral agent is 3-chloro-6-[3,6-dihydro-4-(3-methylphenyl)-1(2H)-pyridinyl]pyridazine; 3-chloro-6-[3-[3-(trifluoromethyl)phenyl]-1-pyrrolidinyl]pyridazine; 3-methyl-6-[3-[3-(trifluoromethyl)phenyl]-1-pyrrolidinyl]pyridazine; 3-iodo-6-[3-[3-(trifluoromethyl)phenyl]-1-pyrrolidinyl]pyridazine; 3-bromo-6-[3-[3-(trifluoromethyl)phenyl]-1-pyrrolidinyl]pyridazine: 3-[3,6-dihydro-4-(3-methylphenyl)-1(2H)-pyridinyl]6-methoxypyridazine; 3-methoxy-6-[4-(3-methylphenyl)-1-piperazinyl]pyridazine; or 3-bromo-6-[4-(3-methylphenyl)-1-piperazinyl]pyridazine.

15. A composition according to claim 2 wherein the anti-rhinoviral agent is a compound having the formula

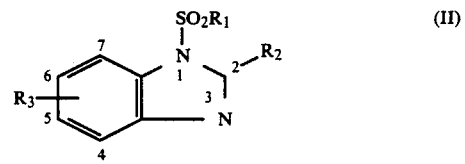

wherein $R_1$ is $C_1$–$C_5$ alkyl, $C_3$–$C_7$ cycloalkyl, phenyl, furyl, thienyl, thiazol-2-yl, 2-acetamido-4-methylthiazol-5-yl, 1,3,4-thiadiazol-2-yl, 2-methyl-1,3,4-thiadiazol-5-yl, 2-methylamino-1,3,4-thiadiazol-5-yl or $R_4R_5N$—, wherein $R_4$ and $R_5$ are independently $C_1$–$C_3$ alkyl or $R_4$ and $R_5$, when taken together with the nitrogen atom to which they are attached, are pyrrolidino, piperidino or morpholino;

$R_2$ is amino, formamido, acetamido, propionamido or butyramido;

$R_3$ is hydroxy, $C_2$–$C_8$ alkanoyloxy, phenylacetoxy, α-$C_1$–$C_7$ alkyl-α-hydroxybenzyl or benzoyloxy; or 1,3-dithiolan-2-yl, 1,3-dithian-2-yl, tetrazol-5yl, 1-($C_1$–$C_4$alkyl)tetrazol-5-yl, 1,3,4-oxadiazol-2-yl, or 2-($C_1$–$C_4$alkyl)oxadiazol-5-yl; or

wherein $R_4$ is hydrogen, $C_1$–$C_7$alkyl, $C_3$–$C_7$cycloalkyl, ($C_3$–$C_7$ cycloalkyl)methyl, 1-($C_3$–$C_7$ cycloalkyl)ethyl, benzyl, phenyl or phenyl substituted by $C_1$–$C_4$ alkyl, $C_1$–$C_4$ alkoxy, chloro, bromo, iodo, nitro or trifluoromethyl; or Z=C($R_4$)—, wherein Z is hydroxyimino, $C_1$–$C_4$ alkoxyimino, $C_1$–$C_4$ acyloxyimino, benzyloxyimino, benzoyloxyimino, hydrazono, thiocarbamylhydrazono, carboxymethoxyimino, methoxycarbonylhydrazono, ethoxycarbonylhydrazono, carbamylhydrazono, $C_1$–$C_4$alkoxycarbonylethylcarbonyloxyimino, benzyloxycarbonylaminomethylcarbonyloxyimino, p-nitrobenzyloxycarbonylethylcarbonyloxyimino, phthalimidomethylcarbonyloxyimino, 2-(2-benzyloxycarbonyl-5-oxoisoxazolidin-4-yl)ethylcarbonyloxyimino or $C_1$–$C_7$ alkylidene; and $R_3$ is at the 5 or 6 position.

16. A composition according to claim 2, wherein the anti-rhinoviral agent is a compound of formula

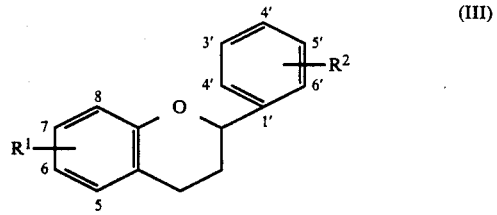

or, where appropriate, a pharmaceutically-acceptable salt thereof, wherein $R^1$ and $R^2$ represent halogen atoms or nitro, cyano, trifluoromethyl, $C_{1-6}$alkyl, lower alkoxyl, $C_{1-6}$alkylamino, amino or hydroxyl groups.

17. A composition according to claim 2, wherein the anti-rhinoviral agent is a compound of formula

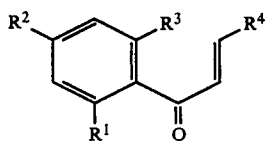 (IV)

wherein
$R^1$ represents hydroxy, acyloxy derived from an aliphatic acid having 2–18 carbon atoms or a heterocyclic carboxylic acid containing nitrogen atom(s), lower alkoxycarbonyloxy, aminoacyloxy or carboxyalkanoyloxy;
$R^2$ represents lower alkoxy;
$R^3$ represents hydrogen or lower alkoxy; and
$R^4$ represents phenyl which may be substituted by one or more substituents selected from the group consisting of $C_{1-6}$alkyl, lower alkoxy, benzyloxy, allyloxy, alkylthio, dialkylamino, amino, cyano, hydroxy, halo and alkylenedioxy; or pyridyl, furyl, thienyl or pyrrolyl which may be substituted by $C_{1-6}$alkyl.

18. A composition according to claim 2, wherein the anti-rhinoviral agent is a compound of formula

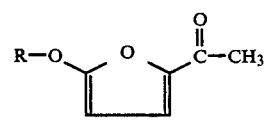 (V)

wherein
R is a straight or branched saturated hydrocarbon chain having from 12 to 16 carbon atoms or a straight or branched unsaturated hydrocarbon chain having from 12 to 16 carbon atoms and from 1 to 4 double bond.

19. A composition according to claim 2, wherein the anti-rhinoviral agent is a compound of formula

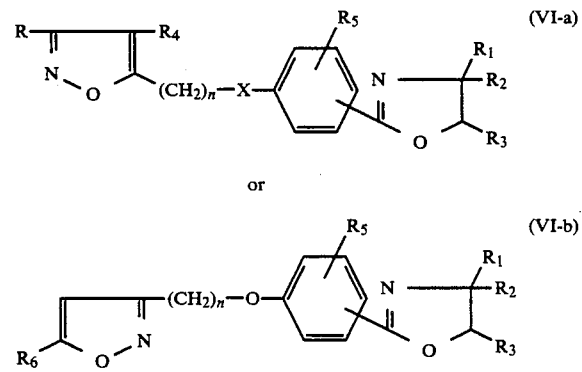

wherein:
R, $R_1$, $R_2$, $R_3$ and $R_4$ are each hydrogen or alkyl of 1 to 3 carbon atoms which may be substituted by hydroxy, lower alkanoyloxy, lower alkoxy, chloro, or N=Z, wherein N=Z is amino, lower alkanoylamino, lower alkylamino, di-lower alkylamino, 1-pyrrolidinyl, 1-piperidinyl or 4-morpholinyl; with the proviso that R is other than hydrogen;
$R_5$ is hydrogen, lower-alkyl, halogen, nitro, loweralkoxy, lower-alkylthio or trifluoromethyl;

$R_6$ is alkyl of 1 to 3 carbon atoms;
X is O or a single bond; and
n is an integer from 3 to 9;
and the pharmaceutically acceptable acid-addition salts thereof.

20. A spray containing a composition according to claim 2 in a liquid form.

21. A method for treating a rhinoviral infection in a mammal which comprises administering to said mammal an effective amount of a pharmaceutical composition which comprises a cyclodextrin and an anti-rhinoviral agent.

22. A method according to claim 21, wherein said rhinoviral infection is in the nasal passages of said mammal and said administration is to the nasal passages.

23. A method according to claim 21, wherein said rhinoviral infection is a common cold.

24. A method according to claim 21, wherein said infection is in the eye of said mammal and said administering is to the eye.

25. A method according to claim 21, with the proviso that if the cyclodextrin is a γ-cyclodextrin ether or mixed ether, wherein the ether substituents are $C_{1-6}$alkyl, hydroxy$C_{1-6}$alkyl, carboxy$C_{1-6}$alkyl or ($C_{1-6}$alkyloxycarbonyl)$C_{1-6}$alkyl, then said agent is not of the following formula:

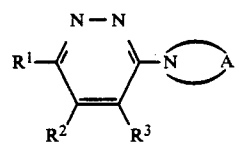

a pharmaceutically-acceptable acid-addition salt and/or a stereochemically isomeric form and/or a tautomeric form thereof,
wherein
$R^1$ is a member selected from the group consisting of hydrogen, halo, 1H-imidazol-1-yl, lower alkyloxy, aryloxy, aryllower alkyloxy, lower alkylthio, arylthio, hydroxy, mercapto, amino, lower alkylsulfinyl, lower alkylsulfonyl, cyano, lower alkyloxycarbonyl, lower alkylcarbonyl, and lower alkyl;
$R^2$ and $R^3$ are, each independently, members selected from the group consisting of hydrogen and lower alkyl, or $R^2$ and $R^3$ combined may form a bivalent radical of formula —CH=CH—CH=CH—;
A is a bivalent radical of formula:

—CH=N—CH=CH— (a),

—CH=N—CH=CH—, (a)

$$-C_mH_{2m}-\overset{R^4}{\underset{|}{N}}-C_nH_{2n}-,$$ (b)

$$-C_mH_{2m}-\overset{R^5}{\underset{\diagdown}{C}}\overset{R^6}{\underset{\diagup}{}}-C_nH_{2n}-, \text{ or}$$ (c)

$$-C_{m-1}H_{2(m-1)}-\overset{R^7}{\underset{|}{C}}=\overset{R^8}{\underset{|}{C}}-C_nH_{2n}-;$$ (d)

wherein one of the hydrogen atoms within the radical $C_mH_{2m}$, $C_{m-1}H_{2(m-1)}$ or $C_nH_{2n}$ may be replaced by lower alkyl or aryl;

m and n are, each independently, integers of from 1 to 4 inclusive, the sum of m and n being 3, 4 or 5;

R⁴ is a member selected from the group consisting of hydrogen; lower alkyl; aryl; thiazolyl; pyrimidinyl; quinolinyl; lower alkylcarbonyl; lower alkyloxycarbonyl; aryllower alkyl; diaryllower alkyl; phenyl being substituted with arylcarbonyl; pyridinyl which may be substituted with cyano or lower alkyl; cyclohexyl and cyclohexenyl both of which may be substituted with up to two substituents independently selected from the group consisting of cyano and aryl;

R⁵ is hydrogen; lower alkyl; aryl; hydroxy; lower alkyloxy; aryloxy; lower alkyloxy being substituted with morpholine, pyrrolidine or piperidine; amino; (lower alkyloxycarbonyl)amino; arylamino; (aryl)(lower alkyl)amino; (aryllower alkyl)amino; (aryllower alkenyl)amino; (aryllower alkenyl)(lower alkyl)amino; arylcarbonyloxy;

R⁶ is hydrogen; aryl; lower alkyl; (lower alkylcarbonyl amino)lower alkyl, aryllower alkyl; arylcarbonyllower alkyl; aminocarbonyl; arylcarbonyl; arylaminocarbonyl; (aryllower alkyl)carbonyl, lower alkyloxycarbonyl; indolyl; pyridinyl;

R⁷ and R⁸ are, each independently, members selected from the group consisting of hydrogen, lower alkyl, aryl, aryllower alkyl and pyridinyl;

wherein aryl is phenyl which may be substituted with up to 3 substituents, each independently selected from the group consisting of halo, lower alkyl, trifluoromethyl, nitro, amino, lower alkyloxy, hydroxy and lower alkyloxycarbonyl; thienyl; and naphthalenyl; lower alkyl comprises straight and branch chained saturated hydrocarbon radicals having from 1 to 6 carbon atoms; lower alkenyl comprises alkenyl radicals having from 2 to 6 carbon atoms.

26. A method according to claim 25 wherein the anti-rhinoviral agent is a hydrophobic nonpeptide agent.

27. A method according to claim 26 wherein the cyclodextrin is a β- or γ-cyclodextrin.

28. A method according to claim 27 wherein the cyclodextrin is a β- or γ-cyclodextrin ether or mixed ether wherein the ether substituents are $C_{1-6}$alkyl, hydroxy$C_{1-6}$alkyl, carboxy$C_{1-6}$alkyl or ($C_{1-6}$alkyloxycarbonyl)$C_{1-6}$alkyl.

29. A method according to claim 28 wherein the ether substituents are $C_{1-3}$alkyl, hydroxy$C_{2-4}$alkyl or carboxy$C_{1-2}$alkyl.

30. A method according to claim 29 wherein the ether substituents are methyl, ethyl, hydroxyethyl, hydroxypropyl, hydroxybutyl, carboxymethyl or carboxyethyl.

31. A method according to claim 29 wherein the DS is in the range of 0.125 to 3 and the MS is in the range of 0.125 to 10.

32. A method according to claim 29 wherein the molar ratio of cyclodextrin:anti-rhinoviral agent in said composition is in the range from 1:1 to 5:1.

33. A method according to claim 29 wherein the said cyclodextrin is present in said composition in an amount of about 5 to 15% weight percent.

34. A method according to claim 26 wherein the said anti-rhinoviral agent is a compound having the formula

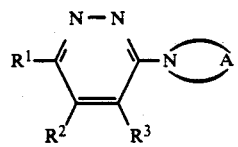

a pharmaceutically-acceptable acid-addition salt and/or a stereochemically isomeric form and/or a tautomeric form thereof wherein R¹ is hydrogen, halo, 1H-imidazol-1-yl, $C_{1-6}$alkyloxy, aryloxy, aryl$C_{1-6}$alkyloxy, $C_{1-6}$alkylthio, arylthio, hydroxy, mercepto, amino, $C_{1-6}$alkylsulfinyl, $C_{1-6}$alkylsulfonyl, cyano, $C_{1-6}$alkyloxycarbonyl, $C_{1-6}$alkylcarbonyl or $C_{1-6}$alkyl;

R² and R³ are, each independently, hydrogen or $C_{1-6}$alkyl; or R² and R³ combined may form a bivalent radical of formula —CH=CH—CH=CH—;

A is a bivalent radical of formula:

—CH=N—CH=CH— (a),

—$C_mH_{2m}$—N(R⁴)—$C_nH_{2n}$— (b),

—$C_mH_{2m}$—C(R⁵R⁶)—$C_nH_{2n}$— (c), or

—$C_{m-1}H_{2(m-1)}$—C(R⁷)=C(R⁸)—$C_nH_{2n}$— (d);

wherein one of the hydrogen atoms within the radical $C_mH_{2m}$, $C_{m-1}H_{2(m-1)}$ or $C_nH_{2n}$ may be replaced by $C_{1-6}$alkyl or aryl;

m and n are, each independently, integers of from 1 to 4 inclusive, the sum of m and n being 3, 4 or 5;

R⁴ is hydrogen; $C_{1-6}$alkyl; aryl; thiazolyl; pyrimidinyl; quinolinyl; $C_{1-6}$alkylcarbonyl; $C_{1-6}$alkyloxycarbonyl; aryl$C_{1-6}$alkyl; diaryl$C_{1-6}$alkyl; phenyl being substituted with arylcarbonyl; pyridinyl which may be substituted with cyano or $C_{1-6}$alkyl; cyclohexyl or cyclohexenyl both of which may be substituted with up to two substituents independently selected from cyano and aryl;

R⁵ is hydrogen; $C_{1-6}$alkyl; aryl; hydroxy; $C_{1-6}$alkyloxy; aryloxy; $C_{1-6}$alkyloxy being substituted with morpholine, pyrrolidine or piperidine; amino; ($C_{1-6}$alkyloxycarbonyl)amino; arylamino; (aryl)($C_{1-6}$alkyl)amino; (aryl$C_{1-6}$alkyl)amino; (aryl$C_{2-6}$ alkenyl)amino; (aryl$C_{3-6}$ alkenyl)($C_{1-6}$alkyl)amino; or arylcarbonyloxy;

R⁶ is hydrogen; aryl; $C_{1-6}$alkyl; ($C_{1-6}$alkylcarbonylamino)$C_{1-6}$alkyl, aryl$C_{1-6}$alkyl; arylcarbonyl$C_{1-6}$alkyl; aminocarbonyl; arylcarbonyl; arylaminocarbonyl; (aryl$C_{1-6}$alkyl)carbonyl; $C_{1-6}$alkyloxycarbonyl; indolyl; or pyridinyl;

R⁷ and R⁸ are, each independently, hydrogen, $C_{1-6}$alkyl, aryl, aryl$C_{1-6}$alkyl or pyridinyl;

wherein aryl is phenyl which may be substituted with up to 3 substituents, each independently selected from halo, $C_{1-6}$alkyl, trifluoromethyl, nitro, amino, $C_{1-6}$alkyloxy, hydroxy and $C_{1-6}$alkyloxycarbonyl; thienyl; and naphthalenyl.

35. A method according to claim 34 wherein the said anti-rhinoviral agent is 3-chloro-6-[3,6-dihydro-4-(3-methylphenyl)-1(2H)-pyridinyl]pyridazine;
3-chloro-6-[3-[3-(trifluoromethyl)phenyl]-1-pyrrolidinyl]pyridazine;
3-methyl-6-[3-[3-(trifluoromethyl)phenyl]-1-pyrrolidinyl]pyridazine;

3-iodo-6-[3-[3-(trifluoromethyl)phenyl]-1-pyrrolidinyl]pyridazine;

3-bromo-6-[3-[3-(trifluoromethyl)phenyl]-1-pyrrolidinyl]pyridazine;

3-[3,6-dihydro-4-(3-methylphenyl)-1(2H)-pyridinyl]-6-methoxypyridazine;

3-methoxy-6-[4-(3-methylphenyl)-1-piperazinyl]pyridazine; or 3-bromo-6-[4-(3-methylphenyl)-1-piperazinyl]pyridazine.

36. A method according to claim 26 wherein the said anti-rhinoviral agent is selected from the group consisting of enviroxime, 4'6-dichloroflavan, 4'-ethoxy-2'-hydroxy-4,6'-dimethylchalcone, 1-(5-tetradecyloxy-2-furanyl)ethanone and 5-[7-[4-(4,5-dihydro-2-oxazolyl)phenoxy]heptyl]-3-methylisoxazole.

* * * * *

UNITED STATES PATENT AND TRADEMARK OFFICE
CERTIFICATE OF CORRECTION

PATENT NO. : 4,956,351

DATED : September 11, 1990

INVENTOR(S) : Jean L. Mesens et al.

It is certified that error appears in the above-identified patent and that said Letters Patent is hereby corrected as shown below:

Claim 1, column 15, line 26, "H" should be --H--.

Claim 1, column 15, line 62, "cyclohenyl" should be --cyclohexyl--.

Claim 13, column 17, line 4, "H" should be --H--.

Claim 25, column 20, line 40, "H" should be --H--.

Signed and Sealed this

Eighteenth Day of August, 1992

Attest:

DOUGLAS B. COMER

Attesting Officer

Acting Commissioner of Patents and Trademarks